United States Patent
Ignatyev et al.

(10) Patent No.: US 9,399,650 B2
(45) Date of Patent: Jul. 26, 2016

(54) METHOD FOR PRODUCING SALTS HAVING MONOFLUORO-TRICYANOBORATE ANIONS

(71) Applicant: MERCK PATENT GMBH, Darmstadt (DE)

(72) Inventors: Nikolai (Mykola) Ignatyev, Duisburg (DE); Jan Arke Peter Spenger, Rommerskirchen (DE); Johannes Landmann, Amorbach (DE); Maik Finze, Kleinrinderfeld (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/898,410

(22) PCT Filed: Jun. 6, 2014

(86) PCT No.: PCT/EP2014/001551
§ 371 (c)(1),
(2) Date: Dec. 14, 2015

(87) PCT Pub. No.: WO2014/198401
PCT Pub. Date: Dec. 18, 2014

(65) Prior Publication Data
US 2016/0130286 A1  May 12, 2016

(30) Foreign Application Priority Data
Jun. 14, 2013 (DE) .......................... 10 2013 009 959

(51) Int. Cl.
*C07F 5/02* (2006.01)

(52) U.S. Cl.
CPC ........................................ *C07F 5/02* (2013.01)

(58) Field of Classification Search
CPC ......................................................... C07F 5/02
See application file for complete search history.

(56) References Cited

PUBLICATIONS

Bernhardt et al. The reactions of M[BF4] (M = Li, K) and (C2H4)2O.BF3 with (CH3)3SiCN. Formation of M[BFx(CN)4-x] (M = Li, K; x = 1, 2) and (CH3)3SiNCBFx(CN)3-x, (x = 0, 1), Zeitschrift fuer Anorganische and Allgemeine Chemie, 2003, vol. 629, pp. 677-685.*
International Search Report for PCT/EP2014/001551 dated Sep. 9, 2014.
Bernahardt, E. et al., The reactions of M[BF4] (M=Li, K) and (C2H5)2O.BF3 with (CH3)3SiCN. Formation of M [BFx(CN)4-x] (M=Li, K; x=1,2) and CH3)3SiNCBFx(CN)3-x, x= 0,1).

* cited by examiner

*Primary Examiner* — Joseph Kosack
(74) *Attorney, Agent, or Firm* — Millen, White, Zelano & Branigan, P.C.

(57) ABSTRACT

The invention relates to a method for producing alkali metal salts having monofluoro-tricyanoborate anions from alkali metal tetrafluoroborates.

10 Claims, No Drawings

METHOD FOR PRODUCING SALTS HAVING MONOFLUORO-TRICYANOBORATE ANIONS

The invention relates to a process for the preparation of alkali metal salts having monofluorotricyanoborate anions from alkali metal tetrafluoroborates.

Alkali metal salts having monofluorotricyanoborate anions are suitable starting materials for the preparation of ionic liquids having monofluorotricyanoborate anions. The use of ionic liquids of this type is manifold, as described, for example, in WO 2004/072089 or in WO 2012/041437. They are suitable, for example, as electrolyte component for electrochemical cells, in particular for dye solar cells.

The preparation of alkali metal monofluorotricyanoborates can be carried out, for example, by reaction of an alkali metal cyanide with boron trifluoride etherate, as described in WO 2004/072089.

Alternatively, alkali metal monofluorotricyanoborates can be prepared by reaction of an alkali metal tetrafluoroborate with a trialkylsilyl cyanide. The reaction of a tetrafluoroborate with trimethylsilyl cyanide is described, for example, in B. H. Hamilton et al., Chem. Commun., 2002, 842-843 or in E. Bernhardt et al., Z. Anorg. Allg. Chem. 2003, 629, 677-685.

The trialkylsilyl cyanide can also be prepared in situ for the preparation of the alkali metal monofluorotricyanoborates. Many preparation methods have been described for the synthesis of trialkylsilyl cyanide.

Trialkylsilyl cyanide can be prepared, for example, from an alkali metal cyanide and a trialkylsilyl chloride. EP 76413 describes that this reaction was carried out in the presence of an alkali metal iodide and in the presence of N-methylpyrrolidone.

EP 40356 describes that this reaction was carried out in the presence of a heavy-metal cyanide.

WO 2008/102661 describes that this reaction was carried out in the presence of iodine and zinc iodide.

WO 2011/085966 describes that this reaction can be carried out in the presence of an alkali metal iodide or fluoride and optionally iodine. Preference is given here to the use of sodium cyanide and sodium iodide or potassium cyanide and potassium iodide, where the alkali metal iodide is preferably added in a molar amount of 0.1 mol, based on 1 mol of alkali metal cyanide and trialkylsilyl chloride. In general, this process for the preparation is based on the description by M. T. Reetz, I. Chatziiosifidis, Synthesis, 1982, p. 330; J. K. Rasmussen, S. M. Heilmann and L. R. Krepski, The Chemistry of Cyanotrimethylsilane in G. L. Larson (Ed.) "Advances in Silicon Chemistry", Vol. 1, p. 65-187, JAI Press Inc., 1991 or WO 2008/102661.

However, there continues to be a need for economical improved alternative synthetic methods for the preparation of alkali metal monofluorotricyanoborates.

The object of the present invention is therefore to develop an improved preparation process which starts from readily accessible and comparatively cheap starting materials, where at the same time the reaction time is reduced and/or the purity of the end products is increased.

Surprisingly, it has been found that the purity of the end product can be increased and/or the reaction time can be reduced if the reaction with a trialkylsilyl cyanide takes place in the presence of a trialkylchlorosilane, trialkylbromosilane and/or trialkyliodosilane.

The invention therefore relates to a process for the preparation of compounds of the formula I $$[Me]^+[BF(CN)_3]^-  \qquad I,$$

where
Me denotes an alkali metal,
by reaction of a compound of the formula II

$$[Me^1]^+[BF_n(CN)_{4-n}]^-  \qquad II,$$

where $Me^1$ denotes an alkali metal, which may be identical to or different from Me, and
n denotes 2, 3 or 4,
with a trialkylsilyl cyanide in the presence of a trialkylsilyl chloride, trialkylsilyl bromide and/or trialkylsilyl iodide, where the alkyl groups of the trialkylsilyl cyanide or trialkylsilyl halide in each case, independently of one another, denote a linear or branched alkyl group having 1 to 10 C atoms, where the conditions of the reaction are selected in such a way that both the water content and also the oxygen content are a maximum of 1,000 ppm, and subsequent metal cation exchange in the case where $Me^1$ does not correspond to Me.

Alkali metals are the metals lithium, sodium, potassium, caesium or rubidium.

In compounds of the formula I, Me is preferably sodium or potassium, particularly preferably potassium.

Accordingly, the process according to the invention is preferably suitable for the synthesis of sodium monofluorotricyanoborate or potassium monofluorotricyanoborate.

The compounds of the formula II are commercially available, in particular for compounds of the formula II where n=4, or they are accessible by known synthetic processes.

The preparation of the compounds of the formula II where n=2 and n=3, as described above or preferably described, can be carried out, for example, by reaction of an alkali metal cyanide with boron trifluoride etherate, as described in WO 2004/072089.

In the compounds of the formula II, $Me^1$ can be an alkali metal selected from the group lithium, sodium, potassium, caesium or rubidium, which is selected independently of the alkali metal of the end product of the formula I. $Me^1$ in formula II may be identical to or different from Me in formula I.

In compounds of the formula II, $Me^1$ is preferably sodium or potassium. In compounds of the formula II, $Me^1$ is particularly preferably sodium.

A linear or branched alkyl group having 1 to 10 C atoms is, for example, methyl, ethyl, n-propyl, isopropyl, n-butyl, sec-butyl, tert-butyl, n-pentyl, n-hexyl, n-heptyl, n-octyl, ethylhexyl, n-nonyl or n-decyl.

Trialkylsilyl cyanides are commercially available or are accessible by known synthetic processes.

The alkyl groups of the trialkylsilyl cyanide may be identical or different. The alkyl groups of the trialkylsilyl cyanide have 1 to 10 C atoms, preferably 1 to 8 C atoms, particularly preferably 1 to 4 C atoms. The alkyl groups of the trialkylsilyl cyanide are preferably identical in the case of alkyl groups having 1 to 4 C atoms. An alkyl group of the trialkylsilyl cyanide is preferably different if it is an alkyl group of 5 to 10 C atoms or of 5 to 8 C atoms. Suitable examples of trialkylsilyl cyanides are trimethylsilyl cyanide, triethylsilyl cyanide, triisopropylsilyl cyanide, tripropylsilyl cyanide, octyldimethylsilyl cyanide, butyldimethylsilyl cyanide, t-butyldimethylsilyl cyanide or tributylsilyl cyanide.

Particular preference is given to the use of trimethylsilyl cyanide, which is commercially available or can also be prepared in situ.

In the process according to the invention, the trialkylsilyl cyanide, as described above or described as preferred or selected from the group trimethylsilyl cyanide, triethylsilyl cyanide, triisopropylsilyl cyanide, tripropylsilyl cyanide, octyldimethylsilyl cyanide, butyldimethylsilyl cyanide, t-butyldimethylsilyl cyanide or tributylsilyl cyanide, is not prepared in situ.

The trialkylchlorosilane, trialkylbromosilane or trialkyliodosilane is commercially available or can be prepared by standard processes. Trialkylbromosilane or trialkyliodosilane can be prepared in situ from a trialkylchlorosilane and an alkali metal bromide or alkali metal iodide.

Trialkylsilyl chlorides (or synonymously trialkylchlorosilanes), trialkylsilyl bromides (synonymously trialkylbromosilanes) and/or trialkylsilyl iodides (synonymously trialkyliodosilanes) which are suitable for the process according to the invention have alkyl groups which are in each case, independently of one another, linear or branched and have 1 to 10 C atoms.

The alkyl groups of the trialkylsilyl halide may be identical or different. The alkyl groups of the trialkylsilyl halide preferably have 1 to 8 C atoms, particularly preferably 1 to 4 C atoms. The alkyl groups of the trialkylsilyl halide are preferably identical in the case of alkyl groups having 1 to 4 C atoms. An alkyl group of the trialkylsilyl halide is preferably different if it is an alkyl group of 5 to 10 C atoms or of 5 to 8 C atoms.

The trialkylsilyl halide is preferably a trialkylsilyl chloride.

Suitable trialkylsilyl chlorides are trimethylsilyl choride (or synonymously trimethylchlorosilane), triethylsilyl chloride, triisopropylsilyl chloride, tripropylsilyl chloride, octyldimethylsilyl chloride, butyldimethylsilyl chloride, t-butyldimethylsilyl chloride or tributylsilyl chloride. Particular preference is given to the use of trimethylsilyl chloride. Very particular preference is given to the use of trimethylsilyl chloride alone.

Suitable trialkylbromosilanes are trimethylbromosilane (or synonymously trimethylsilyl bromide), triethylsilyl bromide, triisopropylsilyl bromide, tripropylsilyl bromide, octyldimethylsilyl bromide, butyldimethylsilyl bromide, t-butyldimethylsilyl bromide or tributylsilyl bromide. Particular preference is given to the use of trimethylsilyl bromide in a mixture with trimethylsilyl chloride.

Suitable trialkyliodosilanes are trimethyliodosilane (or synonymously trimethylsilyl iodide), triethylsilyl iodide, triisopropylsilyl iodide, tripropylsilyl iodide, octyldimethylsilyl iodide, butyldimethylsilyl iodide, t-butyldimethylsilyl iodide or tributylsilyl iodide. Particular preference is given to the use of trimethylsilyl iodide in a mixture with trimethylsilyl chloride.

The trialkylsilyl halide or a mixture of trialkylsilyl halides, as described above or described as preferred, is particularly preferably employed in a total amount of 1 to 20 mol %, based on the amount of trialkylsilyl cyanide employed. The trialkylsilyl halide or a mixture of trialkylsilyl halides is particularly preferably employed in a total amount of 3 to 12 mol %, based on the amount of trialkylsilyl cyanide employed. The trialkylsilyl halide or a mixture of trialkylsilyl halides is very particularly preferably employed in a total amount of 7 to 11 mol %, based on the amount of trialkylsilyl cyanide employed.

The reaction can be carried out both in an open apparatus and also in a closed apparatus.

It is preferred to mix the starting materials in an inert-gas atmosphere whose oxygen content is a maximum of 1000 ppm. It is particularly preferred if the oxygen content is less than 500 ppm, very particularly preferably a maximum of 100 ppm.

The water content of the reagents and of the inert-gas atmosphere is a maximum of 1000 ppm. It is particularly preferred if the water content of the reagents and of the atmosphere is less than 500 ppm, very particularly preferably a maximum of 100 ppm.

The conditions with respect to the water content and oxygen content do not apply to the work-up after successful reaction of the compound of the formula II with the trialkylsilyl cyanide.

The invention therefore furthermore relates to the process, as described above, where the trialkylsilyl halide or a mixture of trialkylsilyl halides is employed in a total amount of 1 to 20 mol %, based on the amount of trialkylsilyl cyanide employed.

In the process according to the invention, it is furthermore preferred if the reaction of the reactants is followed by a purification step in order to separate the end product of the formula I, as described above, off from by-products or reaction products.

Suitable purification steps include the separation of readily volatile components by distillation or condensation, extraction with an organic solvent or a combination of these methods. Each known separation method can be used for this purpose or combined.

The invention therefore furthermore relates to the process, as described above, characterised in that the reaction is followed by a purification step.

Should metal cation exchange be necessary after the reaction of the compound of the formula II with the reactants indicated, as described above and below, has taken place, since the corresponding alkali metal cation Me for the target product of the formula I is not yet present in the reaction mixture, it is preferred in an embodiment of the invention if the metal cation exchange takes place during the purification step.

The metal cation exchange is preferably an alkali metal cation exchange. A preferred method for the metal cation exchange or preferably the alkali metal cation exchange, is, for example, the reaction of the reaction mixture obtained with a corresponding carbonate $(Me)_2CO_3$ and/or a corresponding hydrogencarbonate $MeHCO_3$, where Me corresponds to the alkali metal Me of the desired end product of the formula I.

The reaction mixture obtained from the reaction is preferably cooled to room temperature, and all volatile components are separated off in vacuo. The solid obtained is subsequently preferably mixed with aqueous hydrogen peroxide solution (35%), optionally water, and the corresponding carbonate $(Me)_2CO_3$ and/or the corresponding hydrogencarbonate $MeHCO_3$, where Me corresponds to the alkali metal Me of the desired end product of the formula I. The excess peroxide is subsequently decomposed by addition of a corresponding alkali metal disulfite and extracted with a suitable organic solvent.

Suitable solvents are ethers, such as tetrahydrofuran, diethyl ether, methyl t-butyl ether or dimethoxyethane, or acetone. Tetrahydrofuran or acetone is particularly preferably used. The alkali metal in the corresponding disulfite preferably corresponds to the alkali metal Me of the desired end product of the formula I.

In an alternative method of purification, the reaction mixture is cooled to room temperature and filtered under inert-gas atmosphere, or the supernatant solution is poured off. The solid is subsequently dried in vacuo, and any trialkylsilyl cyanide coordinated to the alkali metal monofluorotricyanoborate is separated off. The solid which remains is then taken up in water and hydrogen peroxide solution and mixed with the corresponding carbonate $(Me)_2CO_3$ and/or the corresponding hydrogencarbonate $MeHCO_3$, where Me corresponds to the alkali metal Me of the desired end product of the formula I. The further work-up is carried out as described above.

Irrespective of which purification method is selected, as described above, the end product of the formula I can be precipitated by addition of an organic solvent in which the end product is insoluble, or the solvent used for the extraction is distilled off. The end product obtained is then dried and characterised by conventional methods.

The invention therefore furthermore relates to the process according to the invention, as described above, where the metal cation exchange, preferably the alkali metal cation exchange, takes place during the purification step.

The invention therefore furthermore relates to the process according to the invention, as described above, where the metal cation exchange is carried out by reaction with the compound $(Me_2)CO_3$ and/or the compound $MeHCO_3$, where Me corresponds to the alkali metal Me of the desired end product of the formula I.

In an embodiment of the process according to the invention, as described above, the reaction of the compound of the formula II, as described above or described as preferred below, takes place in the presence of an organic solvent. Suitable solvents are acetonitrile, propionitrile or benzonitrile. A particularly suitable solvent for the reaction described is acetonitrile.

In an embodiment of the process according to the invention, as described above, the reaction of the compound of the formula II, as described above or described as preferred below, takes place without an organic solvent.

The reaction mixture in this embodiment of the process according to the invention is formed by the compound of the formula II, the trialkylsilyl cyanide, the trialkylsilyl chloride and the trialkylsilyl fluoride formed.

The invention therefore furthermore relates to the process according to the invention, as described above, where the reaction of the compound of the formula II, as described above or described as preferred below, takes place in the presence of an organic solvent or without an organic solvent.

In a preferred embodiment of the process according to the invention, a compound of the formula II in which n denotes 2 or 4 is employed.

The invention therefore furthermore relates to the process according to the invention, as described above or described in its embodiments, characterised in that a compound of the formula II in which n denotes 2 or 4 is employed.

In a particularly preferred embodiment of the process according to the invention, a compound of the formula II in which n denotes 4 is employed.

The invention therefore furthermore relates to the process according to the invention, as described above or described in its embodiments, characterised in that a compound of the formula II in which n denotes 4 is employed.

The process according to the invention, as described above, described in its embodiments or described as preferred, is carried out either in an open apparatus or in a closed apparatus.

If the reaction is carried out in an open reaction apparatus as apparatus, suitable measures must be taken in order to remove the trialkylsilyl fluoride formed from the reaction. Measures of this type are known to the person skilled in the art. Suitable measures are described in the example part.

If the reaction is carried out in a closed reaction apparatus as apparatus, the reaction takes place at a maximum pressure of 2.5 bar.

The invention therefore furthermore relates to the process, as described above, characterised in that the reaction is carried out in an open or closed apparatus.

In a preferred embodiment of the process according to the invention, as described above, described in its embodiments, or described as preferred, the reaction of the compound of the formula II with trialkylsilyl cyanide in the presence of a trialkylsilyl halide or a mixture of trialkylsilyl halides takes place at a reaction temperature of 50° C. to 120° C. The reaction preferably takes place at 60° C. to 100° C.

The invention therefore furthermore relates to the process, as described above, characterised in that the reaction of the compound of the formula II with trialkylsilyl cyanide takes place at a temperature of 50° C. to 120° C.

The substances obtained are characterised by means of NMR spectra. The NMR spectra are measured on solutions in deuterated acetone-$D_6$ or in $CD_3CN$ on a Bruker Avance 200 spectrometer with deuterium lock. The measurement frequencies of the various nuclei are: $^1H$ (199.93 MHz), $^{19}F$ (188.09 MHz), $^{11}B$ (64.14 MHz). The referencing is carried out using an external reference: $^1H$-NMR: TMS (residual proton signal of acetone-$D_6$: 2.05 ppm); $^{19}F$-NMR: $ClCF_3$, $^{11}B$-NMR: $BF_3$ etherate.

EXAMPLE 1

Synthesis of Sodium Monofluorotricyanoborate; $Na[BF(CN)_3]$

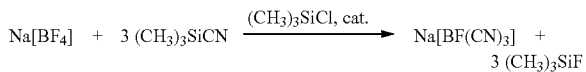

11.0 g (100 mmol) of sodium tetrafluoroborate, $Na[BF_4]$, is initially introduced in a flask with PTFE spindle (Young, London). 100 ml of the mixture of trimethylsilyl cyanide, $(CH_3)_3SiCN$ (75 mol %), trimethylsilyl cloride, $(CH_3)_3SiCl$ (15 mol %) and trimethylsilyl fluoride, $(CH_3)_3SiF$ (10 mol %) (these and similar mixtures are recovered from the reactions described here during work-up) is added to the sodium tetrafluoroborate. The flask is closed, and the reaction mixture is stirred at 90° C. (oil-bath temperature) for 4 hours. 20 ml of fresh trimethylsilyl cyanide and 2 ml of trimethylsilyl chloride are then added, and the reaction mixture is stirred at 80° C. (oil-bath temperature) for a further 5 hours.

All volatile substances are then distilled off, and the residue is dried at 60° C. in vacuo for one day, giving 13.1 g (100 mmol) of $Na[BF(CN)_3]$.

The $^{19}F$- and $^{11}B$-NMR spectra are identical with those of Example 2.

EXAMPLE 2

Synthesis of Potassium Monofluorotricyanoborate; $K[BF(CN)_3]$

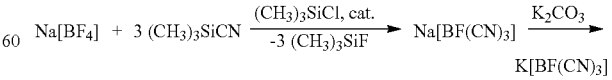

20.0 g (182 mmol) of sodium tetrafluoroborate, $Na[BF_4]$, and 200 ml (1.5 mol) of trimethylsilyl cyanide, $(CH_3)_3SiCN$, are initially introduced, and 20 ml (158 mmol) of trimethylchlorosilane, $(CH_3)_3SiCl$, are added to this suspension. The reaction mixture is heated under reflux (oil-bath temperature 65° C. to 95° C.) for 96 hours. All volatile substances are then distilled off in vacuo. The mixture of trimethylsilyl cyanide, $(CH_3)_3SiCN$, trimethylsilyl chloride, $(CH_3)_3SiCl$, and trimethylsilyl fluoride, $(CH_3)_3SiF$, is collected in a cold trap and can be employed analogously to the mixture in Example 1 in a second synthesis. The residue is taken up in 100 ml of water, and hydrogen peroxide $H_2O_2$ (37% solution, about 200 ml) and $K_2CO_3$ (about 100 g) are carefully added until the solution is virtually no longer coloured. The excess peroxide is destroyed by addition of $K_2S_2O_5$. The water is distilled off, and the residue obtained is extracted with acetone (3×100 ml). The combined organic phases are reduced to 50 ml, and dichloromethane is then added until $K[BF(CN)_3]$ precipitates out. Filtration and drying in vacuo gives 19.8 g (134.8 mmol) of $K[BF(CN)_3]$. The yield is 74%, based on sodium tetrafluoroborate.

$^{19}$F-NMR (solvent: acetone-$D_6$), δ, ppm: −212.08 q, $^1J_{11B, 19F}$=44.4 Hz.

$^{11}$B-NMR (solvent: acetone-$D_6$), δ, ppm: −17.88 d, $^1J_{11B, 19F}$=44.4 Hz.

The spectra correspond to those from the literature [E. Bernhardt, M. Berkei, H. Willner, M. Schürmann, Z. Anorg. Allg. Chem., 2003, 629, 677-685].

Elemental analysis:
found, %: C 24.53, H 0.00, N 27.86:
calculated for $C_3BFN_3K$, %: C 24.52, H 0.00, N 28.59.

EXAMPLE 3

Synthesis of Potassium Monofluorotricyanoborate; $K[BF(CN)_3]$

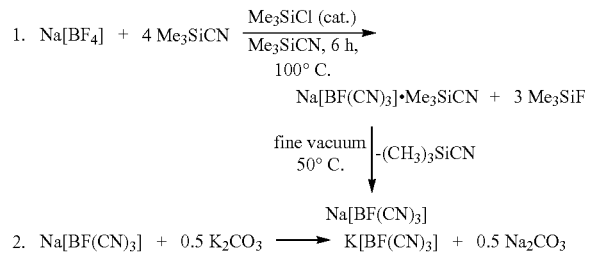

A)
Structure of the apparatus:

A 2 l three-necked flask is fitted with stirrer bar, gas valve, internal thermometer and reflux condenser (No. 1, coolant temperature set to 25° C. using a cryostat). The temperature should not be lower than 25° C., since otherwise $(CH_3)_3SiF$ flows back and the reaction mixture cools excessively; and not higher, since otherwise the catalytically active $(CH_3)_3SiCl$ exits from the reaction mixture through the reflux condenser. A tube is run from this reflux condenser to a further reflux condenser (No. 2, coolant temperature 10° C.) in order to condense the $(CH_3)_3SiF$ exiting through reflux condenser No. 2. This runs into a 500 ml two-necked flask with bubble counter/non-return valve. The 500 ml two-necked flask is cooled to 0° C. using an ice bath. The heat-transfer means used is an aluminium dish (heat-on attachment, Heidolph).

Procedure:
Sodium tetrafluoroborate, $Na[BF_4]$ (50 g, 0.455 mol), is initially introduced in a 2 l three-necked flask, thoroughly inertised, and $(CH_3)_3SiCN$ (1.0 l, 7.5 mol) is subsequently introduced in a counterstream of Ar. $(CH_3)_3SiCl$ (50 ml, 396 mmol) is added to the suspension, and the reaction mixture is heated for 6 hours. The temperature of the aluminium dish is set to 100° C. The temperature of the reaction mixture is about 80-85° C. $(CH_3)_3SiF$ discharged through the reflux condenser (No. 1, 25° C.) is condensed using a reflux condenser (No. 2, 10° C.) and collected in the 500 ml two-necked flask at 0° C. After cooling to room temperature, all volatile constituents of the reddish suspension are distilled off in vacuo (about $10^{-1}$-$10^{-2}$ mbar). The dark-red solid obtained is dried in a fine vacuum at 50° C. to a final pressure of $10^{-3}$ mbar and then taken up in aqueous hydrogen peroxide solution (35%, 50 ml), and $K_2CO_3$ (80 g) is added successively. Excess peroxide is subsequently decomposed by addition of potassium disulfide, and the mixture is then extracted with THF (3×80, 3×50). The combined THF phases are dried using $K_2CO_3$ and subsequently evaporated to a residual volume of about 30-40 ml using a rotary evaporator (bath temperature 50° C.). Addition of $CH_2Cl_2$ (100 ml) causes colourless $K[BF(CN)_3]$ to precipitate out. This is filtered off (pore 4) and dried in a fine vacuum ($10^{-3}$ mbar).

The yield of $K[BF(CN)_3]$ is 49.8 g (0.338 mmol), 74%, based on the borate employed.

$^{19}$F-NMR (solvent: acetone-$D_6$)), δ, ppm: −212.08 q, ($^1J_{11B,19F}$=44.4 Hz). $^{11}$B-NMR (solvent: acetone-$D_6$), δ, ppm: −17.88 d, ($^1J_{11B,19F}$=44.4 Hz).

B)
Structure of the apparatus:

A 2 l three-necked flask is fitted with stirrer bar, dropping funnel with gas valve, internal thermometer and reflux condenser (coolant temperature set to 25° C. using cryostat). The temperature should not be lower, since otherwise $(CH_3)_3SiF$ flows back and the reaction mixture cools excessively, and not higher, since otherwise the catalytically active $(CH_3)_3SiCl$ exits from the reaction mixture.

Procedure:
Sodium tetrafluoroborate, $Na[BF_4]$ (100 g, 911 mmol) is initially introduced in the 2 l three-necked flask, rendered inert, and trimethylsilyl cyanide, $(CH_3)_3SiCN$ (1.2 l, 9.0 mol) is subsequently introduced in a counterstream of Ar. The suspension is warmed to 50° C., and trimethylchlorosilane, $(CH_3)_3SiCl$ (50 ml, 396 mmol), is then added. The reaction mixture is stirred at 50° C. for 1 hour, and the temperature of the reaction mixture is subsequently increased to 85° C. During the heating, further $(CH_3)_3SiCl$ (50 ml, 396 mmol) is added dropwise, and the mixture is stirred for 5 hours. The $(CH_3)_3SiF$ formed is discharged through the reflux condenser. When the reaction is complete, all volatile constituents of the reaction mixture are distilled off under reduced pressure (about $10^{-1}$-$10^{-2}$ mbar). The brown solid obtained is dried in a fine vacuum at 50° C. to a final pressure of $10^{-3}$ mbar and then taken up in aqueous hydrogen peroxide solution (35%, 100 ml), and $K_2CO_3$ (150 g) is added successively. Excess peroxide is subsequently decomposed by addition of potassium disulfide, and the mixture is then extracted with THF (5×80, 5×50). The combined THF phases are dried using $K_2CO_3$ and subsequently evaporated to a residual volume of about 40-50 ml using a rotary evaporator (bath temperature 50° C.). Addition of $CH_2Cl_2$ (150 ml) causes colourless $K[BF(CN)_3]$ to precipitate out. This is filtered off (pore 4) and dried in a fine vacuum ($10^{-3}$ mbar).

The yield of $K[BF(CN)_3]$ is 107.6 g (732 mmol), corresponding to 80%, based on the borate employed.

The NMR data correspond to the data given above.

EXAMPLE 4

Synthesis of Potassium Monofluorotricyanoborate; K[BF(CN)₃]

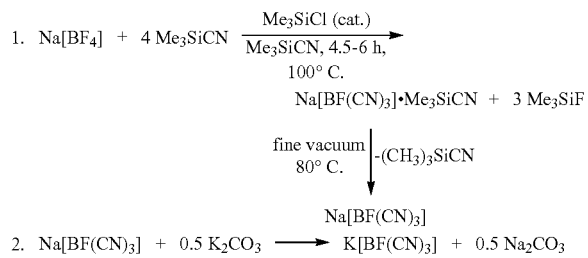

1. Na[BF₄] + 4 Me₃SiCN $\xrightarrow[\substack{Me_3SiCN, 4.5\text{-}6\text{ h,} \\ 100°\text{ C.}}]{Me_3SiCl\text{ (cat.)}}$ Na[BF(CN)₃]·Me₃SiCN + 3 Me₃SiF $\downarrow$ fine vacuum 80° C. | -(CH₃)₃SiCN Na[BF(CN)₃]

2. Na[BF(CN)₃] + 0.5 K₂CO₃ ⟶ K[BF(CN)₃] + 0.5 Na₂CO₃

A)
Sodium tetrafluoroborate, Na[BF₄] (52.5 g, 0.478 mol), is initially introduced in a 1 l round-bottomed flask with glass valve and Teflon spindle (Young, London) and rendered inert. Trimethylsilyl cyanide, (CH₃)₃SiCN (500 ml, 3.75 mol), and trimethylchlorosilane, (CH₃)₃SiCl (50.0 ml, 0.396 mol), are added in a counterstream of argon, and the suspension is warmed at 50° C. for one hour with stirring. The gas phase above the reaction mixture is then removed in vacuo until the reaction mixture begins to boil. The reaction mixture is subsequently heated at 100° C. for 4.5 hours in the sealed flask. The pressure measured is up to 2.5 bar. The cooled suspension is subsequently filtered inert (pore 4), and the pale-pink solid (Na[BF(CN)₃].NCSi(CH₃)₃) is freed from the coordinated trimethylsilyl cyanide in a fine vacuum (10⁻³ mbar) at up to 80° C. The crude product Na[BF(CN)₃] obtained is taken up in water (20 ml), and aqueous hydrogen peroxide solution (35%, 30 ml) is added. K₂CO₃ (80 g) is added successively to the reddish mixture, excess peroxide is decomposed by addition of potassium disulfide The mixture is subsequently extracted with THF (7×80 ml). The combined THF phases are dried using K₂CO₃ and subsequently evaporated to a residual volume of about 30 ml using a rotary evaporator (bath temperature 50° C.). Addition of CH₂Cl₂ (150 ml) causes colourless K[BF(CN)₃] to precipitate out. This is filtered off (pore 4) and dried in a fine vacuum.

The yield of K[BF(CN)₃] is 54.4 g (0.370 mmol), corresponding to 77%, based on the borate employed.

The NMR data correspond to the data given above.

B)
Sodium tetrafluoroborate, Na[BF₄] (120.0 g, 1.09 mol), is initially introduced in a 2 l round-bottomed flask with glass valve and a gas-tight stirring coupling with precision glass drive and PTFE-clad stirring shaft (Bola from Bohlender, Grünsfeld) and rendered inert. Trimethylsilyl cyanide, (CH₃)₃SiCN (1.3 l, 9.75 mol), and trimethylchlorosilane, (CH₃)₃SiCl (100.0 ml, 0.792 mol), are added in a counterstream of argon. The suspension is warmed at 50° C. for one hour. At 50° C., the valve is opened briefly in order to remove the gaseous constituents (Ar, (CH₃)₃SiF). The reaction mixture is then heated at 100° C. for 6 hours in the sealed flask. The pressure measured is up to 2.5 bar. The cooled suspension is subsequently filtered inert (pore 4), and the pale-pink solid (Na[BF(CN)₃].NCSi(CH₃)₃) is freed from the coordinated trimethylsilyl cyanide in a fine vacuum (10⁻³ mbar) at up to 80° C. The crude product Na[BF(CN)₃] obtained is taken up in water (50 ml), and aqueous hydrogen peroxide solution (35%, 50 ml) is added. K₂CO₃ (150 g) is added successively to the reddish mixture, excess peroxide is decomposed by addition of potassium disulfide The mixture is subsequently extracted with THF (10×80 ml). The combined THF phases are dried using K₂CO₃ and subsequently evaporated to a residual volume of about 50 ml using a rotary evaporator (bath temperature 50° C.). Addition of CH₂Cl₂ (200 ml) causes colourless K[BF(CN)₃] to precipitate out. This is filtered off (pore 4) and dried in a fine vacuum.

The yield of K[BF(CN)₃] is 125.4 g (0.85 mmol), corresponding to 78%, based on the borate employed.

The NMR data correspond to the data given above.

EXAMPLE 5

Synthesis of Potassium Monofluorotricyanoborate; K[BF(CN)₃]

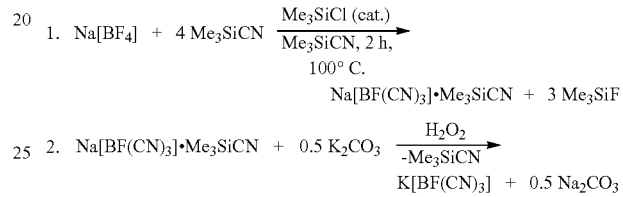

1. Na[BF₄] + 4 Me₃SiCN $\xrightarrow[\substack{Me_3SiCN, 2\text{ h,} \\ 100°\text{ C.}}]{Me_3SiCl\text{ (cat.)}}$ Na[BF(CN)₃]·Me₃SiCN + 3 Me₃SiF 2. Na[BF(CN)₃]·Me₃SiCN + 0.5 K₂CO₃ $\xrightarrow[-Me_3SiCN]{H_2O_2}$ K[BF(CN)₃] + 0.5 Na₂CO₃

Sodium tetrafluoroborate, Na[BF₄] (20.0 g, 182 mmol), is dried in a fine vacuum in a flask with a glass valve and a PTFE spindle (Young, London) and a magnetic stirrer bar and subsequently taken up in trimethylsilyl cyanide, (CH₃)₃SiCN (220.0 ml, 1.65 mol). Trimethylchlorosilane, (CH₃)₃SiCl (15.0 ml, 119 mmol), is added to the suspension, and the reaction mixture is subsequently heated at 100° C. for 2 hours in the sealed flask. After cooling to room temperature, the reaction solution is poured off from the crystalline precipitate (Na[BF(CN)₃].TMSCN). The solid which remains is dried in a fine vacuum (10⁻³ mbar) at room temperature and subsequently taken up in water (15 ml). K₂CO₃ and H₂O₂ (35%, 5 ml) are added to the solution, which is then stirred at RT (room temperature) for 1 hour. The solution is subsequently evaporated to dryness using a rotary evaporator, and the residue is taken up in THF (50 ml). The THF phase is dried using K₂CO₃, filtered, and the filtrate is evaporated to dryness in vacuo. The colourless solid (K[BF(CN)₃]) obtained is dried overnight in a fine vacuum (10⁻³ mbar).

The yield of K[BF(CN)₃] is 21.46 g (146 mmol), corresponding to 80%, based on the borate employed.

Elemental analysis K[BF(CN)₃]:
calculated, %: C, 24.52; H, 0.00; N, 28.59
found, %: C, 24.96; H, 0.00; N, 28.18
The NMR data correspond to the data given above.

EXAMPLE 6

Synthesis of Potassium Monofluorotricyanoborate; K[BF(CN)₃]

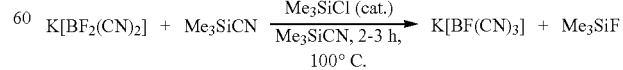

K[BF₂(CN)₂] + Me₃SiCN $\xrightarrow[\substack{Me_3SiCN, 2\text{-}3\text{ h,} \\ 100°\text{ C.}}]{Me_3SiCl\text{ (cat.)}}$ K[BF(CN)₃] + Me₃SiF A)
Potassium difluorodicyanoborate, K[BF₂(CN)₂] (1.0 g, 7.14 mmol), is taken up in trimethylsilyl cyanide, (CH₃)₃SiCN (12.0 ml, 89.98 mmol), in a flask with a glass valve and a PTFE spindle (Young, London) and a magnetic stirrer bar, and trimethylchlorosilane, $(CH_3)_3SiCl$ (1.0 ml, 7.91 mmol), is subsequently added. The reaction mixture is heated at 100° C. for 2 hours in the sealed flask and subsequently evaporated to dryness in vacuo ($3 \times 10^{-3}$ mbar). The solid which remains is taken up in $H_2O_2$ (35% aqueous solution, 10 ml), and $K_2CO_3$ (3 g) is added to the solution. After 1 hour, all volatile constituents are removed in vacuo, and the solid obtained is suspended in acetone (15 ml). The suspension is dried using $K_2CO_3$ (5 g) and filtered (frit pore 4). The filtrate is evaporated to about 3 ml in vacuo, and addition of $CH_2Cl_2$ (15 ml) causes $K[BF(CN)_3]$ to precipitate out. This is filtered off and dried in a fine vacuum ($3 \times 10^{-3}$ mbar).

The yield of $K[BF(CN)_3]$ is 0.9 g (6.12 mmol), 86%, based on the borate employed.

The NMR data correspond to the data given above.

B)

Potassium difluorodicyanoborate, $K[BF_2(CN)_2]$ (5.0 g, 35.73 mmol), is taken up in trimethylsilyl cyanide, $(CH_3)_3SiCN$ (24.0 ml, 179.97 mmol), in a flask with a glass valve and a PTFE spindle (Young, London) and a magnetic stirrer bar, and trimethylchlorosilane, $(CH_3)_3SiCl$ (1.6 ml, 12.66 mmol), is subsequently added. The reaction mixture is heated at 100° C. for 3 hours in the sealed flask and subsequently evaporated to dryness in vacuo ($3 \times 10^{-3}$ mbar). The solid which remains is taken up in $H_2O_2$ (35% aqueous solution, 20 ml), and $K_2CO_3$ (10 g) is added to the solution. After 1 hour, all volatile constituents are removed in vacuo, and the solid obtained is extracted with THF (3×15 ml). The suspension is dried using $K_2CO_3$ (5 g) and filtered (frit pore 4). The filtrate is evaporated to about 3-4 ml in vacuo, and addition of $CHCl_3$ (30 ml) causes $K[BF(CN)_3]$ to precipitate out. This is filtered off and dried in a fine vacuum ($3 \times 10^{-3}$ mbar).

The yield of $K[BF(CN)_3]$ is 4.4 g (29.94 mmol), 84%, based on the borate employed.

The NMR data correspond to the data given above.

The invention claimed is:

1. Process for the preparation of compounds of the formula I $$[Me]^+[BF(CN)_3]^- \quad \quad I,$$

where
Me denotes an alkali metal,
by reaction of a compound of the formula II $$[Me^1]^+[BF_n(CN)_{4-n}]^- \quad \quad II,$$

where $Me^1$ denotes an alkali metal, which may be identical to or different from Me and
n denotes 2, 3 or 4, with a trialkylsilyl cyanide in the presence of a trialkylsilyl chloride, trialkylsilyl bromide and/or trialkylsilyl iodide, where the alkyl groups of the trialkylsilyl cyanide or trialkylsilyl halide in each case, independently of one another, denote a linear or branched alkyl group having 1 to 10 C atoms,
where the conditions of the reaction are selected in such a way that both the water content and also the oxygen content are a maximum of 1,000 ppm, and subsequent metal cation exchange in the case where $Me^1$ does not correspond to Me.

2. Process according to claim 1, characterised in that the trialkylsilyl hal-ideor the mixture of trialkylsilyl halides is employed in a total amount of 1 to 20 mol %, based on the amount of trialkylsilyl cyanide employed.

3. Process according to claim 1, characterised in that the reaction is followed by a purification step.

4. Process according to claim 1, characterised in that the metal cation exchange takes place during the purification step.

5. Process according to claim 1, characterised in that the metal cation exchange is carried out by reaction with the compound $(Me)_2CO_3$ and/or with the compound $MeHCO_3$, where Me corresponds to the alkali metal Me of the compound of the formula I.

6. Process according to claim 1, characterised in that the reaction of the compound of the formula II with trialkylsilyl cyanide takes place in the presence of an organic solvent or without organic solvent.

7. Process according to claim 1, characterised in that a compound of the formula II in which n denotes 2 or 4 is employed.

8. Process according to claim 1, characterised in that a compound of the formula II in which n denotes 4 is employed.

9. Process according to claim 1, characterised in that the reaction is carried out in an open or closed apparatus.

10. Process according to claim 1, characterised in that the reaction of the compound of the formula II with trialkylsilyl cyanide takes place at a temperature of 50° C. to 120° C.

* * * * *